United States Patent [19]

Ferrante et al.

[11] Patent Number: 5,767,156

[45] Date of Patent: Jun. 16, 1998

[54] POLYUNSATURATED FATTY ACIDS AND USES THEREOF

[75] Inventors: Antonio Ferrante, Mount Osmond; Alfred Poulos, Kensington Gardens; Deborah A. Rathjen, Sheidow Park, all of Australia

[73] Assignees: Peptide Technology Limited, Dee Why; Women's and Childrens Hospital Adelaide, North Adelaide, both of Australia

[21] Appl. No.: 647,988

[22] PCT Filed: Oct. 6, 1994

[86] PCT No.: PCT/AU94/00607

§ 371 Date: May 28, 1996

§ 102(e) Date: May 28, 1996

[87] PCT Pub. No.: WO95/09622

PCT Pub. Date: Apr. 13, 1995

[30] Foreign Application Priority Data

Oct. 6, 1993 [AU] Australia ............................ PM1655
May 20, 1994 [AU] Australia ............................ PM5753

[51] Int. Cl.$^6$ ............................................. A61K 31/20
[52] U.S. Cl. .................................................. 514/560
[58] Field of Search .................................... 514/560

[56] References Cited

U.S. PATENT DOCUMENTS 5,034,415 7/1991 Rubin ........................... 514/560
5,178,873 1/1993 Horrobin et al. ............. 514/560
5,502,077 3/1996 Breivik et al. ................ 514/560
5,550,156 8/1996 Kyle ............................. 514/560

FOREIGN PATENT DOCUMENTS

19689/92 1/1993 Australia ........................ 514/560
92/21726 1/1993 Australia ........................ 514/560
367724 5/1990 European Pat. Off. .......... 514/560
2216418 10/1989 United Kingdom ............. 514/560
2216522 10/1989 United Kingdom ............. 514/560

OTHER PUBLICATIONS

Westey et al, Annals of Surgery, vol. 204, pp. 1–8 (1986).

Bromberg et al, Interleukins Lymphokines & Cycokines (1982), pp. 561–567.

Naccarbe et al, J. of Leukocyte Biology, pp. 333–340 (1984).

Bodway et al, J of Biological Chem, vol. 259, pp. 7870–7877 (1984.

Poulos et al, Immunology, vol. 73, pp. 102–108 (1991).

*Primary Examiner*—James H. Reamer
*Attorney, Agent, or Firm*—Nixon & Vanderhye

[57] ABSTRACT

The present invention provides a method of stimulating macrophage, neutrophil and/or monocyte function in a subject. The method involves the administration of an effective amount of a free fatty acid having a 18–24 carbon chain length with 2–6 double bonds. Preferred polyunsaturated fatty acids are 20:4(n-6), 20:3(n-6), 20:5(n-3), 22:6(n-3), 19:2(n-6), 18:3γ(n-6), 23:4(n-6) and 24:4(n-6).

15 Claims, 22 Drawing Sheets

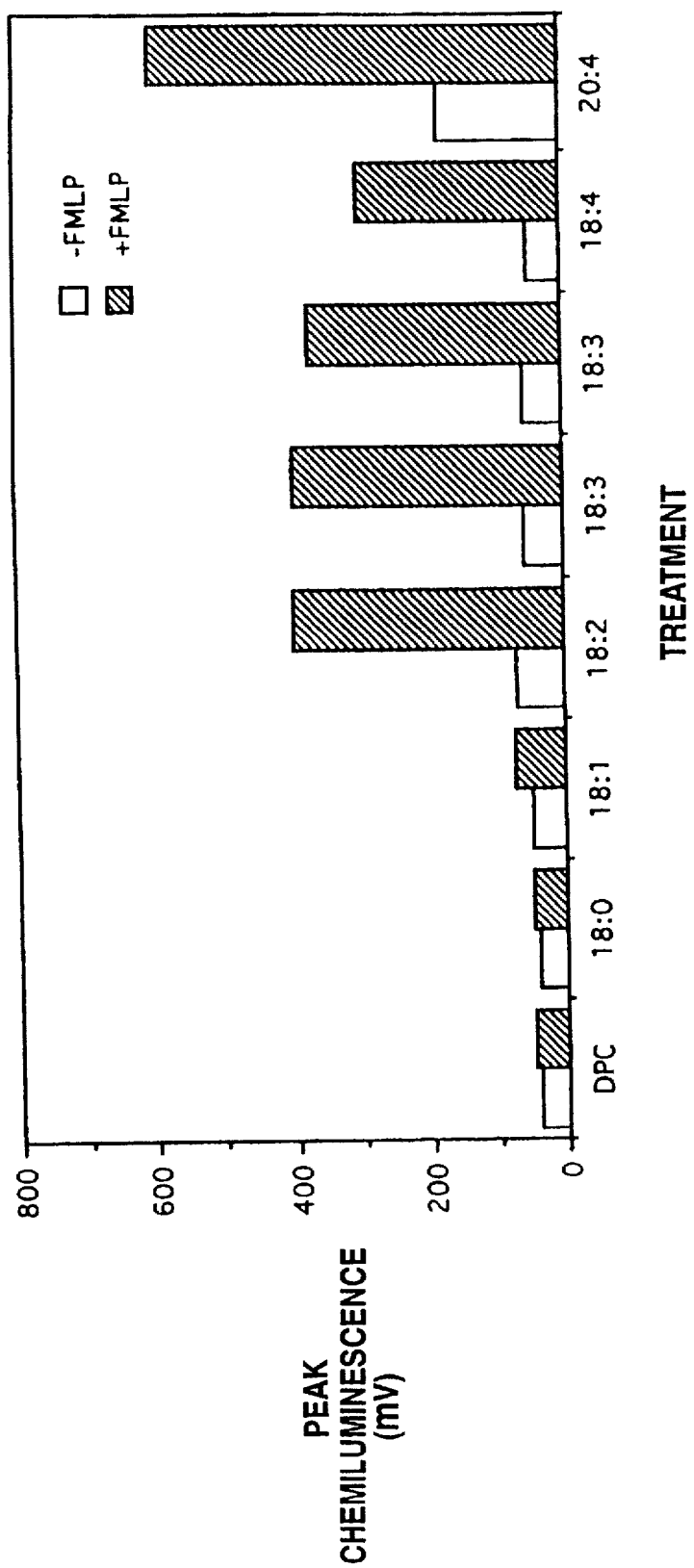

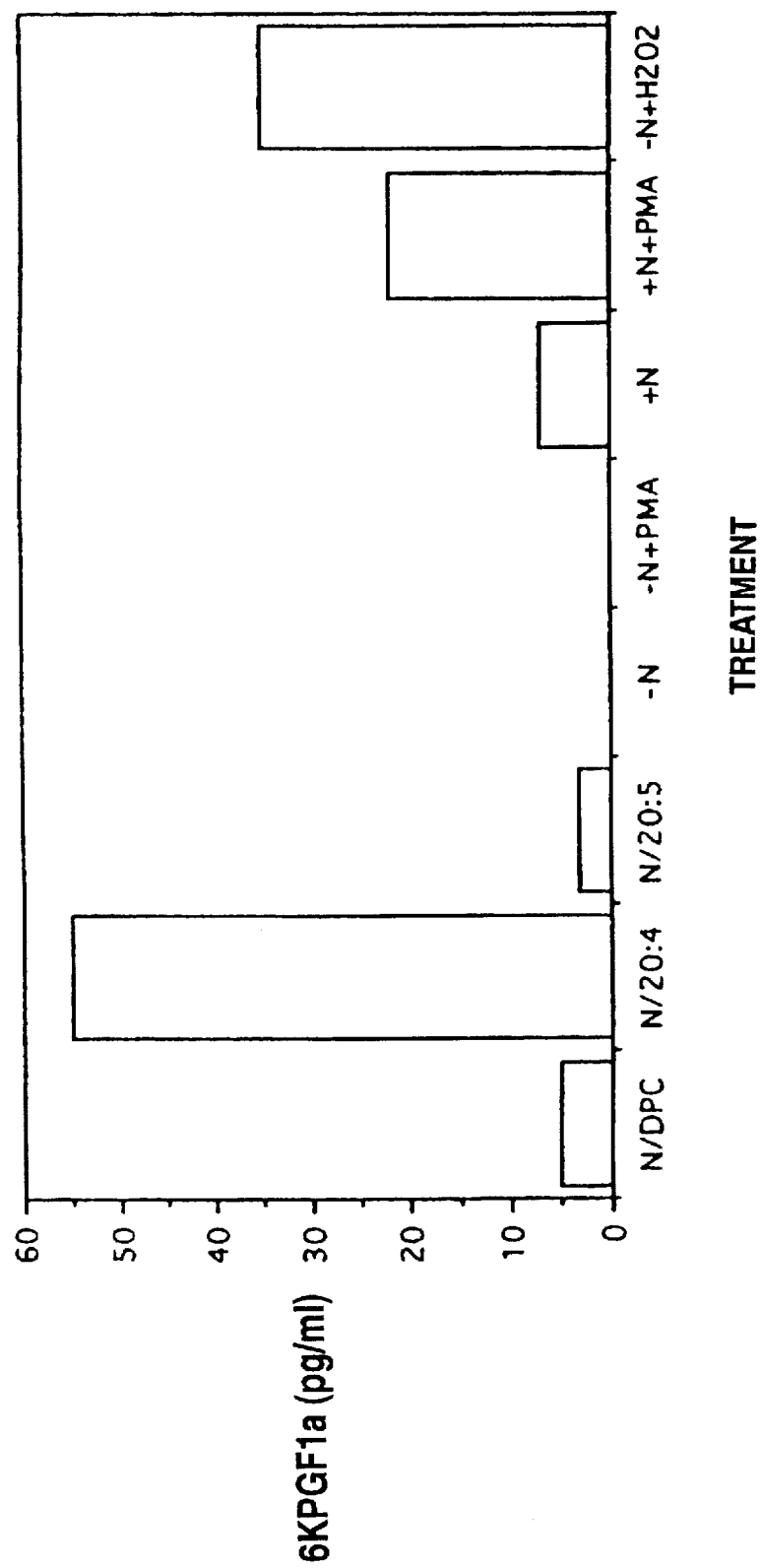

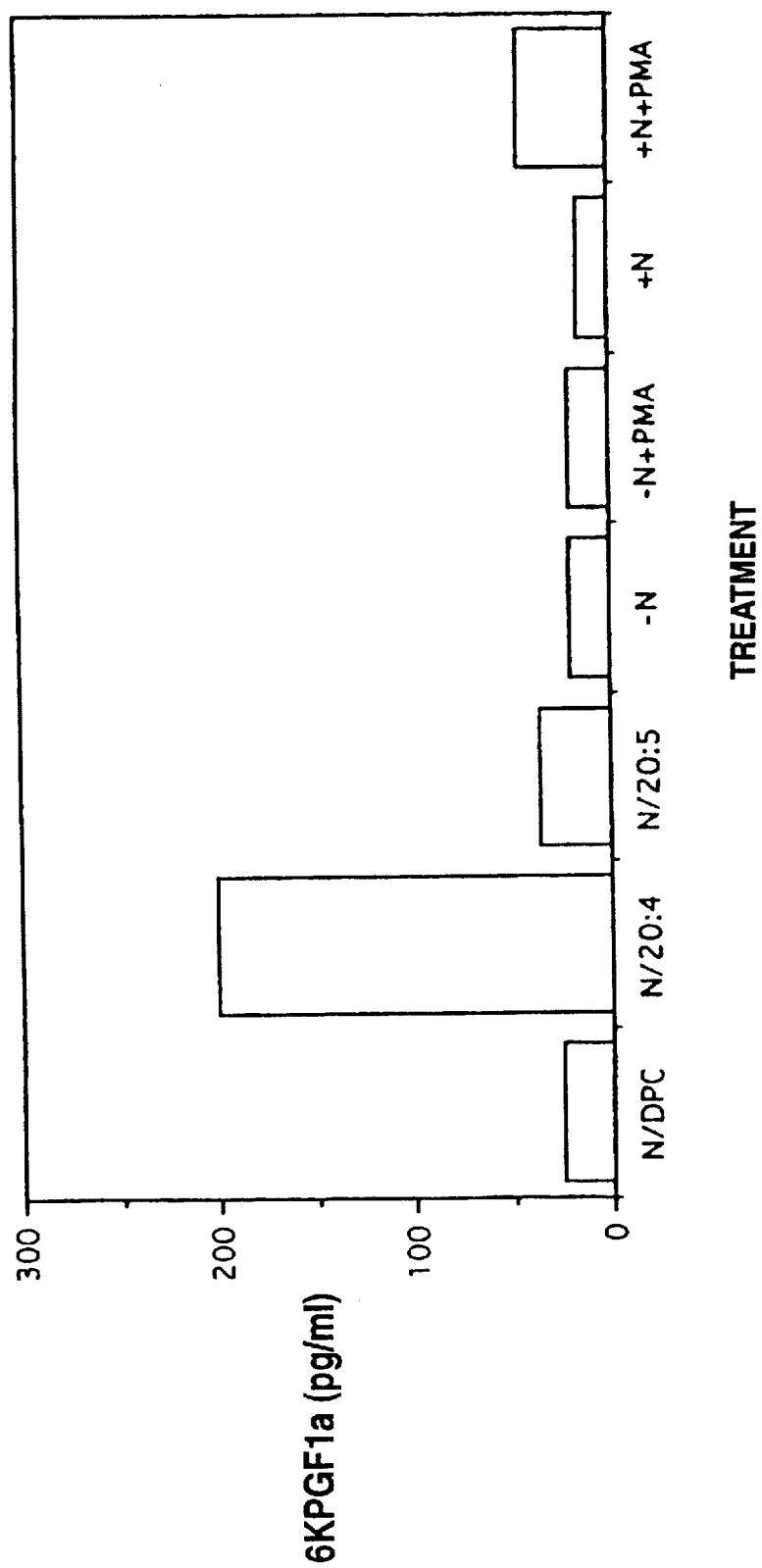

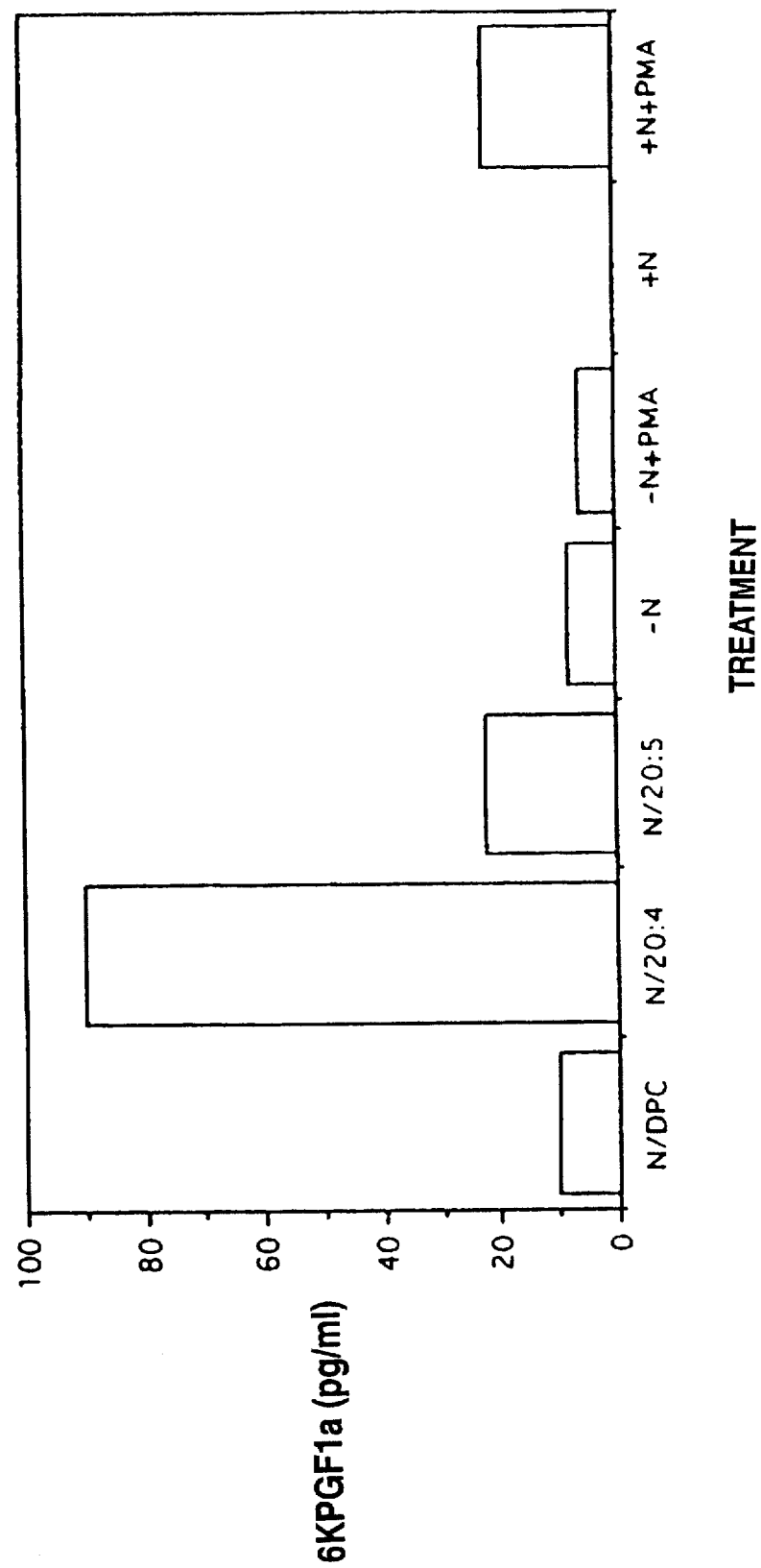

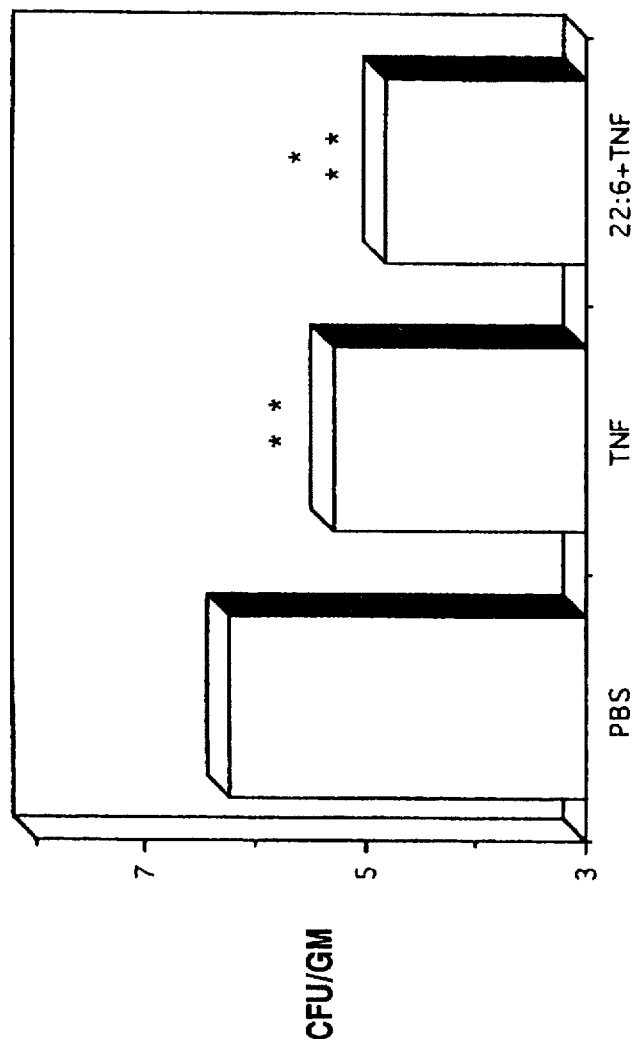

POLYUNSATURATED FATTY ACIDS AND USES THEREOF

The present invention relates to polyunsaturated fatty acids, their use in stimulation of macrophages and neutrophils, and their use as therapeutic agents.

Macrophages play an important role in antimicrobial activity. Macrophage activation results in the killing of bacteria such as *E. coli*, *S. typhimurium*, *L. monocytogenes*, *Legionella pneumophila*, *M. tuberculosis*, *M. Leprae*, Staphylococci, Psuedomonas organisms, *Cryptococcus neoformans*, Chlamydia and *Histoplasma capsulatum*. Macrophages are also involved in anti-viral responses, e.g., against herpes simplex and alpha viruses. Macrophage activation is also a general feature of early parasite infection by parasites, e.g., Plasmodium, Trypanosoma, Leishmania, Helminths e.g., trematodes (Schistosoma) nematodes (Trichenella Tichinosis) etc. They are also thought to have potent anti-fungal activity, e.g., against Candida sp. When activated, macrophages are better able to resist infection by intracellular parasites which normally multiply within them, e.g., Leishmania, *T. cruzi*, and acquire the ability to eliminate already established parasites. The major effector functions of macrophages include: the generation of reactive oxygen intermediates (measured by lucigenin-dependent chemiluminescence and superoxide production), production of reactive nitrogen intermediates, limitation of intracellular iron availability, phagosomal acidification and phagosomal-lysosome fusion, production of defensins. These actions are cytotoxic for many bacteria, parasites and viruses. Stimulated macrophages also kill tumour cells although the mechanisms may not be the same as those involved in microbial killing.

Stimulation of neutrophils results in the generation of oxygen-derived reactive species with release of lysosomal enzymes and other granule proteins (Panettone, J. C. and Ward, P. A. 1992, Am J Pathol 107;396–418). The release of these mediators is coordinated with phagocytosis which leads to microbial killing. It is known that certain PUFA can activate superoxide production by human neutrophils (Badwey et al., 1981, J Biol Chem 256:12640–12643; Badwey et al 1984, J Biol Chem 259:7870–7877, Poulos et al., 1991, Immunol 73:102–108) and that a particular PUFA (docosahexanoeic acid, 22:6, (n-3)) can synergise the superoxide production induced by the bacterial peptide fMLP and the phorbol ester TPA.

While it is known that certain fatty acids can affect the activity of human neutrophils the effects of fatty acids, particularly PUFA, on monocytes and macrophages are less well defined. Dietary deficiency of 20:5n-3 leads to impaired adherence and spreading of macrophages (Lefkowith et al 1991, J. Biol. Chem. 226:1071–1076; Lefkowith et al 1991, J. Immunol. 149:1729–1735). Cultured murine peritoneal macrophages elicited with thioglycollate and cultured in the presence of polyunsaturated fatty acids show increased phagocytosis of unopsonized zymosan (Calder et al 1990, Biochem. J. 269(3):807). Dietary supplementation with fish oil (a mixture of n-3 fatty acids) has yielded conflicting results with respect to superoxide production with either reported enhancement (Berger et al 1992, J. Nutr., 123;225 . 223) or depressing (Fisher et al 1990 Am J. Clin Nutr 51:804–233) of superoxide production by macrophages or monocytes.

Cytokines such as tumour necrosis factor (TNF) and colony stimulating factors (CSFs) have also been shown to activate neutrophils. TNF stimulates enhanced phagocytosis (Shalaby et al, J Immunol 135:2069–2073), enhanced production of superoxide anions (Teujiimoto et al., 1986, Biochem. Biophys. Res Comm 137:1094–1100), release of lysozyme and hydrogen peroxide and causes neutrophil degranulation (Klebanoff et al., 1986 J Immunol 136:4220–4225). Neutrophils also show enchanced microbiocidal and tumourcidal activity when stimulated by TNF (Shalaby et al, 1985 J Immunol 135:2069–2073; Djeu et al., 1986 J Immunon 137:2960–2984; Blanchard et al., 1989 J Leukocyte Biol 45:538–454). The anti-tumour action of TNF may be mediated through the activation of neutrophils (Shau 1986, J Immunol 141-234-340).

Neutrophil function is known to be depressed in a number of viral, bacterial and parasitic infections and may be suppressed in cancer or as a result of associated therapies (Abramson and Mills, 1988, Rev Infect Dis 10:326–341; Ferrante et al., 1989, Immunol Letts 22:301–6; Thorsen et al., 1989 AIDS 3:651–653).

International Patent Application No WO93/00064 discloses that polyunsaturated fatty acids having a carbon chain length of up to 30 carbon atoms have anti-microbial and anti-tumour activity. This reference discloses that a large range of polyunsaturated fatty acids and their derivatives have a direct effect on malarial parasites in vitro and in vivo and on tumour cells in vivo. It is also disclosed in this reference that greater anti-malarial activity is obtained using the oxidized forms of the polyunsaturated fatty acids.

The present inventors have made the novel observation that certain PUFA stimulate microbial killing by neutrophils without deleterious effects on endothelial cells which line the vasulature and which are particularly sensitive to the pro-inflammatory effects of neutrophil activation. Not all PUFA which activate neutrophils have this property since neutrophil activation, as described above, results in the release of inflammatory molecules such as elastase and prostaglandin $I_2$. Release of neutrophil elastase correlates with endothelial cell damage. In addition, the present inventors have shown that this activity is only present in the free polyunsaturated fatty acids and is lost in the hydroxy and hydroperoxy forms. This is in clear contrast to the findings set out in WO93/00084. Further, the inventors have for the first time observed that the action of these PUFAs and cytokines such as TNF are synergistic which may have additional beneficial effects.

The present invention further relates to the observation that particular n-3 and n-6 polyunsaturated fatty acids activate human monocytes and macrophages to produce superoxide. Not only do they stimulate superoxide production by macrophages and monocytes alone but they also prime the cells for enhanced responses to bacterial peptides (e.g., fMLP) or phorbol esters (e.g., PMA). These findings have implications for the therapy of both infection and cancer where macrophage function may be of importance. Many of the functions listed above occur in immunocompromised individuals undergoing chemotherapy, immunotherapy or with debilitating chronic infection (e.g., cystic fibrosis, AIDS). Alcoholism also leads to depressed phagocytic cell activity. These conditions may be particularly suited to treatment with the specified PUFAs.

Accordingly, in a first aspect, the present invention consists in a method of stimulating macrophage, neutrophil and/or monocyte function in a subject, the method comprising administering to the subject an effective amount of the free fatty acid selected from the group of 18 to 24 carbon chain length with 2 to 6 double bonds.

Accordingly, in a second aspect, the present invention consists in a method of stimulating macrophage, neutrophil and/or monocyte function in a subject, the method comprising administering to the subject an effective amount of a free polyunsaturated fatty acid selected from the group consisting of 20:4(n-6), 20:3(n-6), 20:5(n-3), 22:6(n-3), 19:2(n-6), 18:3γ(n-6), 23:4(n-6), and 24:4(n-6).

In a third aspect, the present invention consists in a method of treating a subject having depressed macrophage, neutrophil and/or neutrophil function, the method comprising administering to the subject an effective amount of a free polyunsaturated fatty acid selected from the group consisting of 20:4(n-6), 20:3(n-6), 20:5(n-3), 22:6(n-3), 19:2(n-6), 18:3γ(n-6), 23:4(n-6), and 24:4(n-6).

In a fourth aspect the present invention consists in a method of treating a subject suffering from a microbial infection, the method comprising administering to the subject or effective amount of a free polyunsaturated fatty acid selected from the group consisting of 20:4(n-6), 20:3(n-6), 20:5(n-3), 22:6(n-3), 19:2(n-6), 18:3γ(n-6), 23:4(n-6) and 24:4(n-6).

In a preferred embodiment of the present invention, the polyunsaturated fatty acid is 20:5(n-3).

In a further preferred embodiment of the present invention the microbial infection is a parasitic infection and is most preferably a malarial infection.

In a further preferred embodiment of the present invention the microbial infection is a bacterial infection and is most preferably a *S. aureus, P. aueruginosa, H. influenza* (typable or non-typable), Pneumocystis, or Pneumococcal infection.

In a further preferred embodiment of the present invention the microbial infection is a fungal infection and is most preferably a Candida infection.

In a further embodiment of the present invention the subject having depressed neutrophil function is suffering from acquired immune deficiency syndrome or cancer.

In a further preferred embodiment of the present invention the free polyunsaturated fatty acid is coadministered with TNF or a TNF fragment (e.g., peptides 309, 308, 395 or 419 as described in Australian patent application No 74762/91) or GMCSF, or interferon gamma.

In yet another preferred embodiment of the present invention the polyunsaturated fatty acid is coadministered with anti-tumour, anti-viral or anti-bacterial agents. Examples of such agents include vinblastin, acyclovir, interferon alpha, actinomycin D, AZT, radiotherapy, adriamycin, mytomycin C, cytosine arabinoside, dounorubicin, cysplatin, vincristine, 5-flurouracil and bleomycin.

In a fifth aspect the present invention consists in a method of treating a subject suffering from cystic fibrosis comprising administering to the subject an effective amount of a free polyunsaturated fatty acid selected from the group consisting of 20:4(n-6), 20:3(n-6), 20:5(n-3), 22:6(n-3), 19:2 (n-6), 18:3γ(n-6), 23:4(n-6), and 24:4(n-6).

In a sixth aspect the present invention consists in a method of treating a subject suffering from a granulomatous disease comprising administering to the subject an effective amount of a free polyunsaturated fatty acid selected from the group consisting of 20:4(n-6), 20:3(n-6), 20:5(n-3), 22:6(n-3), 19:2(n-6), 18:3γ(n-6), 23:4(n-6) and 24:4(n-6).

In a further embodiment of the present invention the granulomatous disease is TB, Crohns Disease, sarcoidosis, mycobacterium avian complex, leprosy or syphilis.

In order that the nature of the present invention may be more clearly understood, a preferred form thereof will now be described with reference to the following examples and Figures in which:

FIG. 9 shows ability of various PUFAs to stimulate the respiratory burst of neutrophils;

Figure 10A:
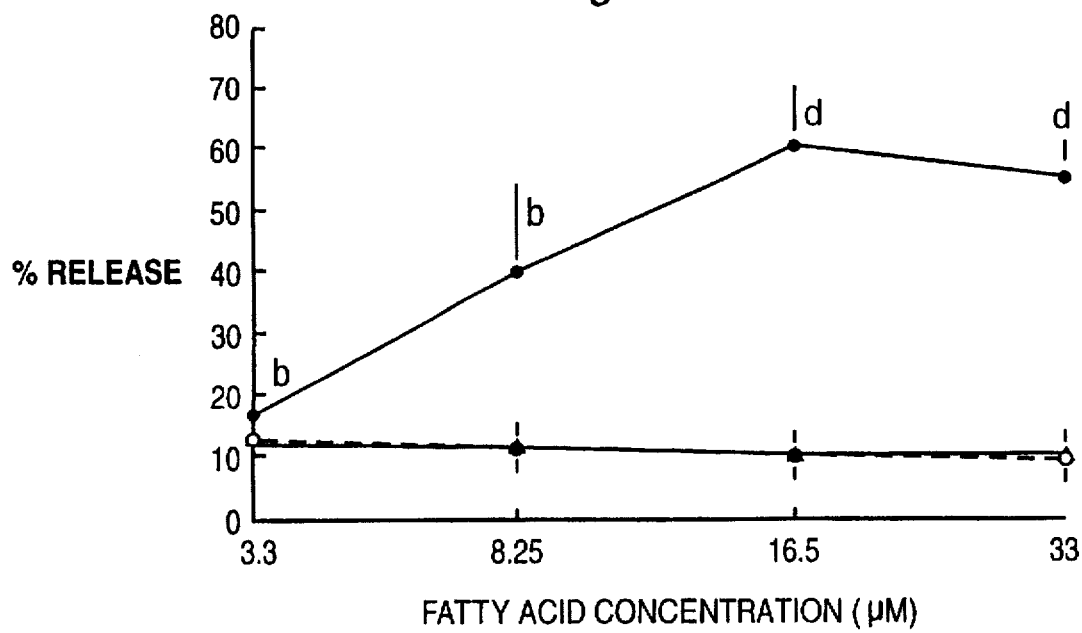
Figure 10B:
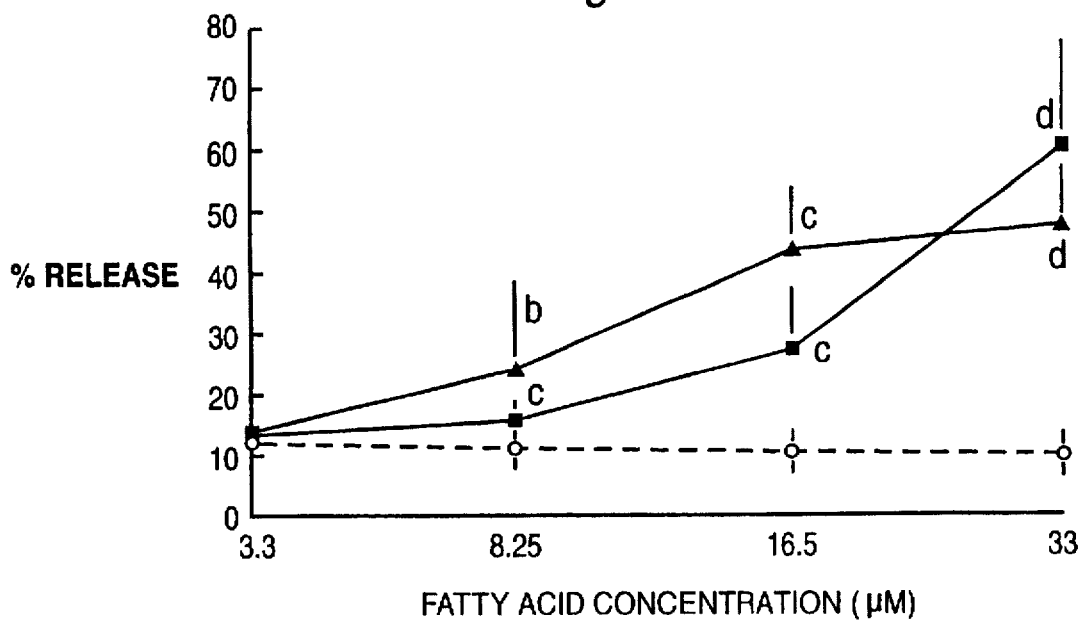
Figure 11A:
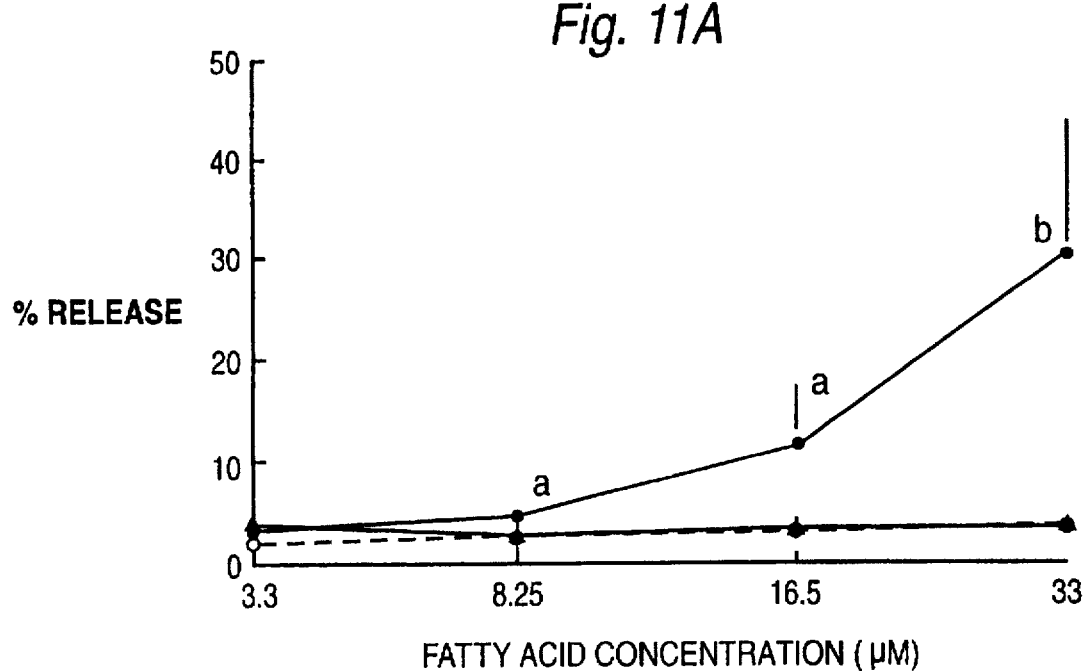
Figure 11B:
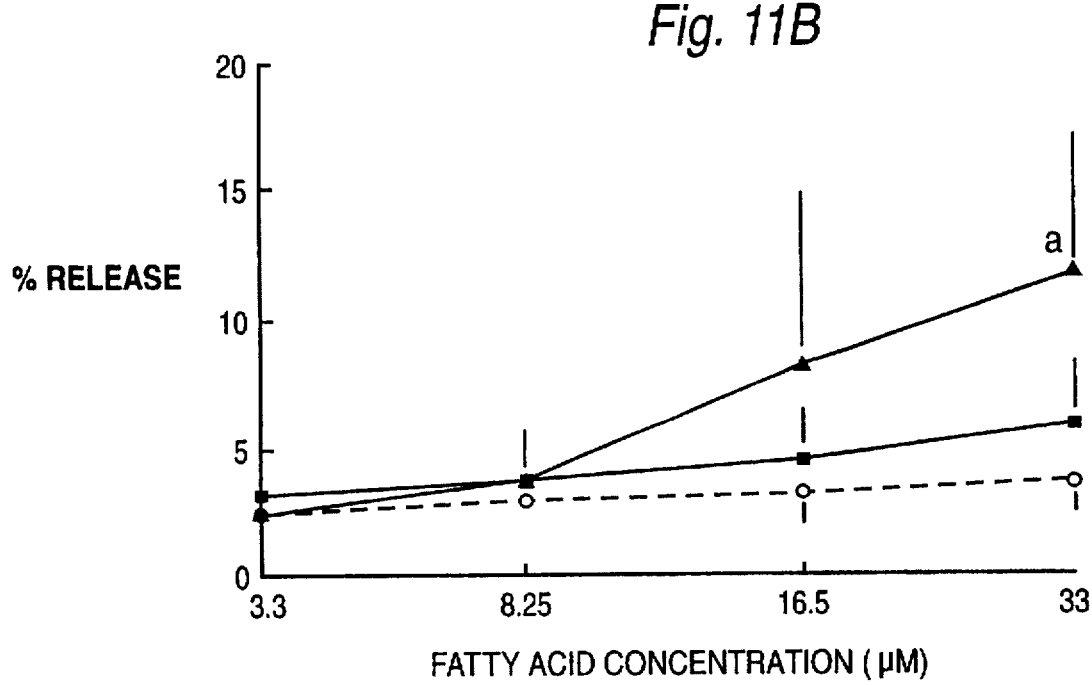
Figure 12A:
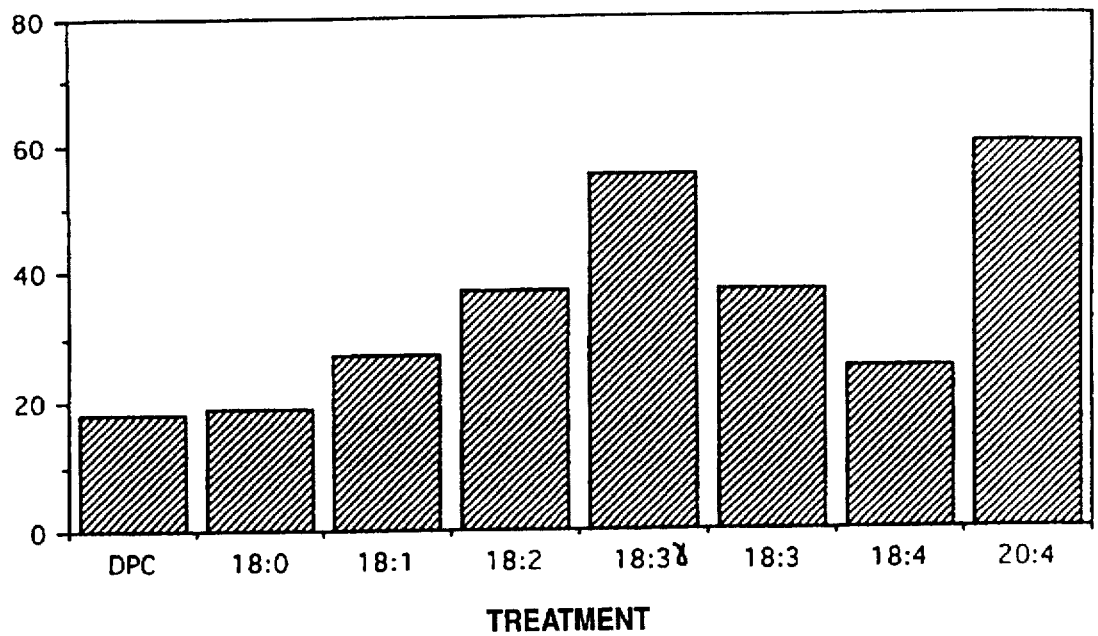
Figure 12B:
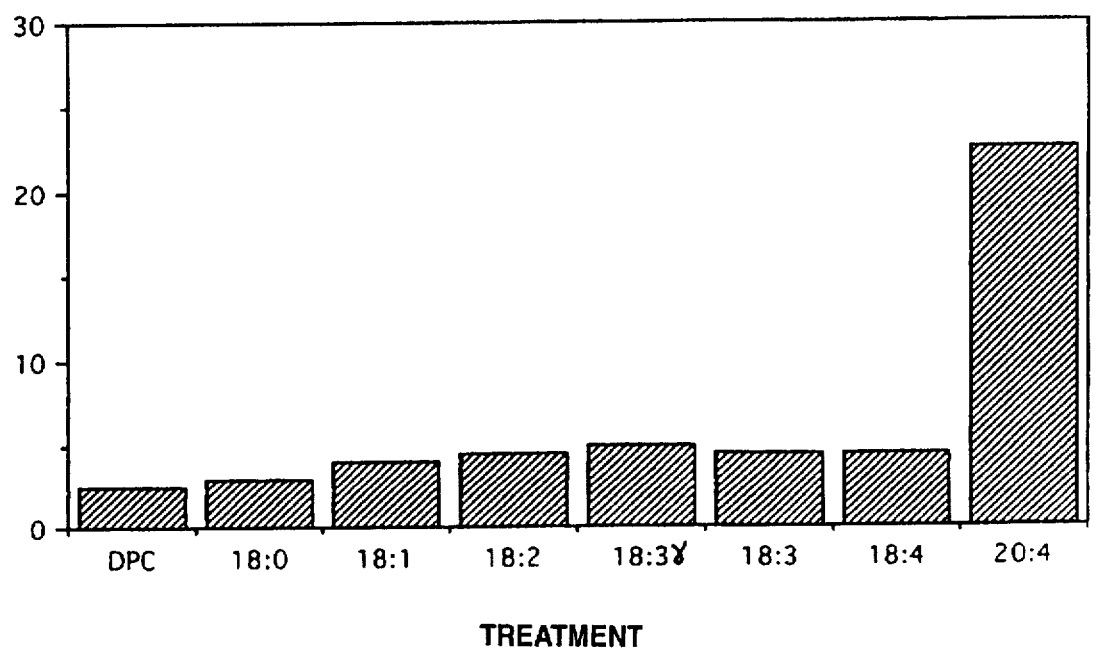
Figure 14:
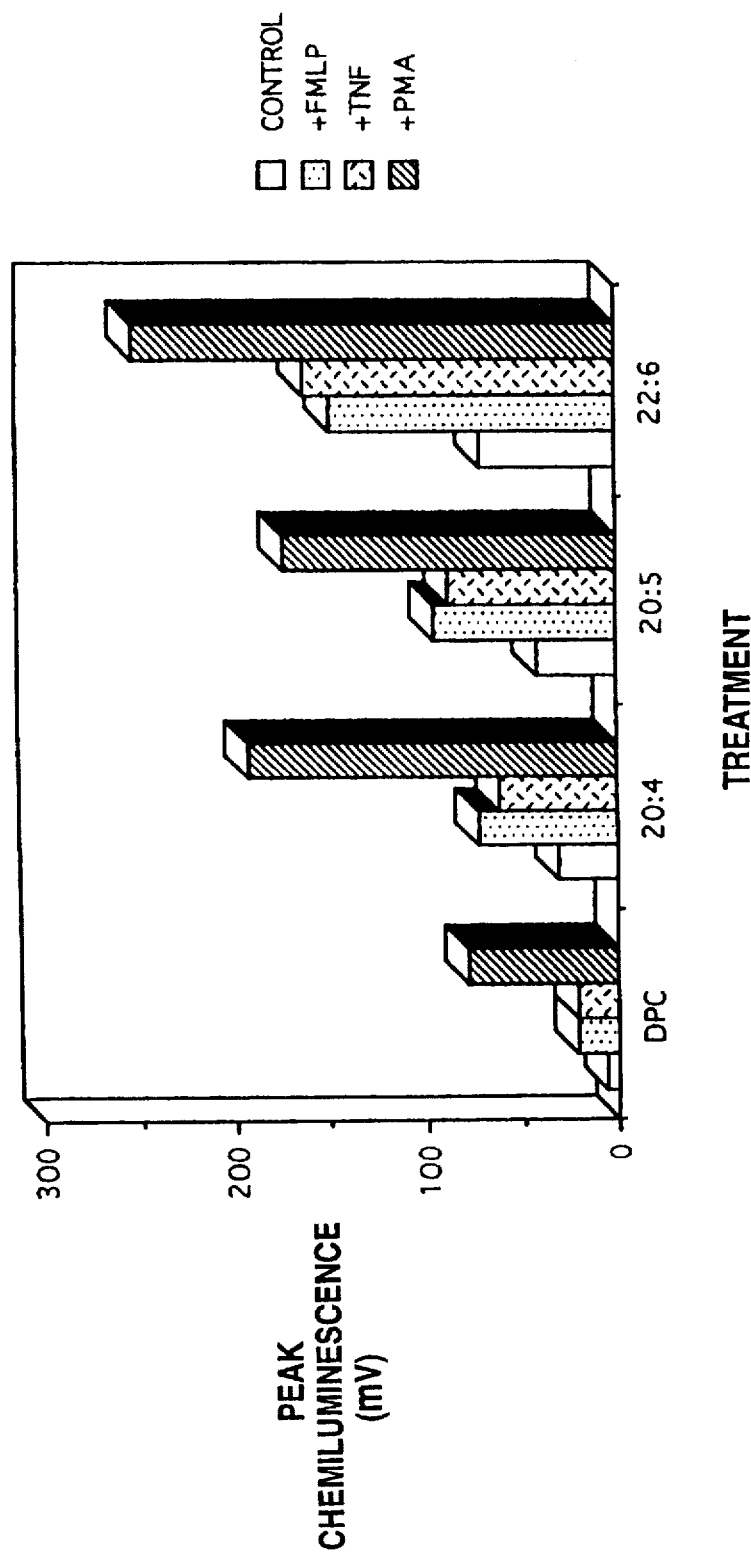
Figure 15:
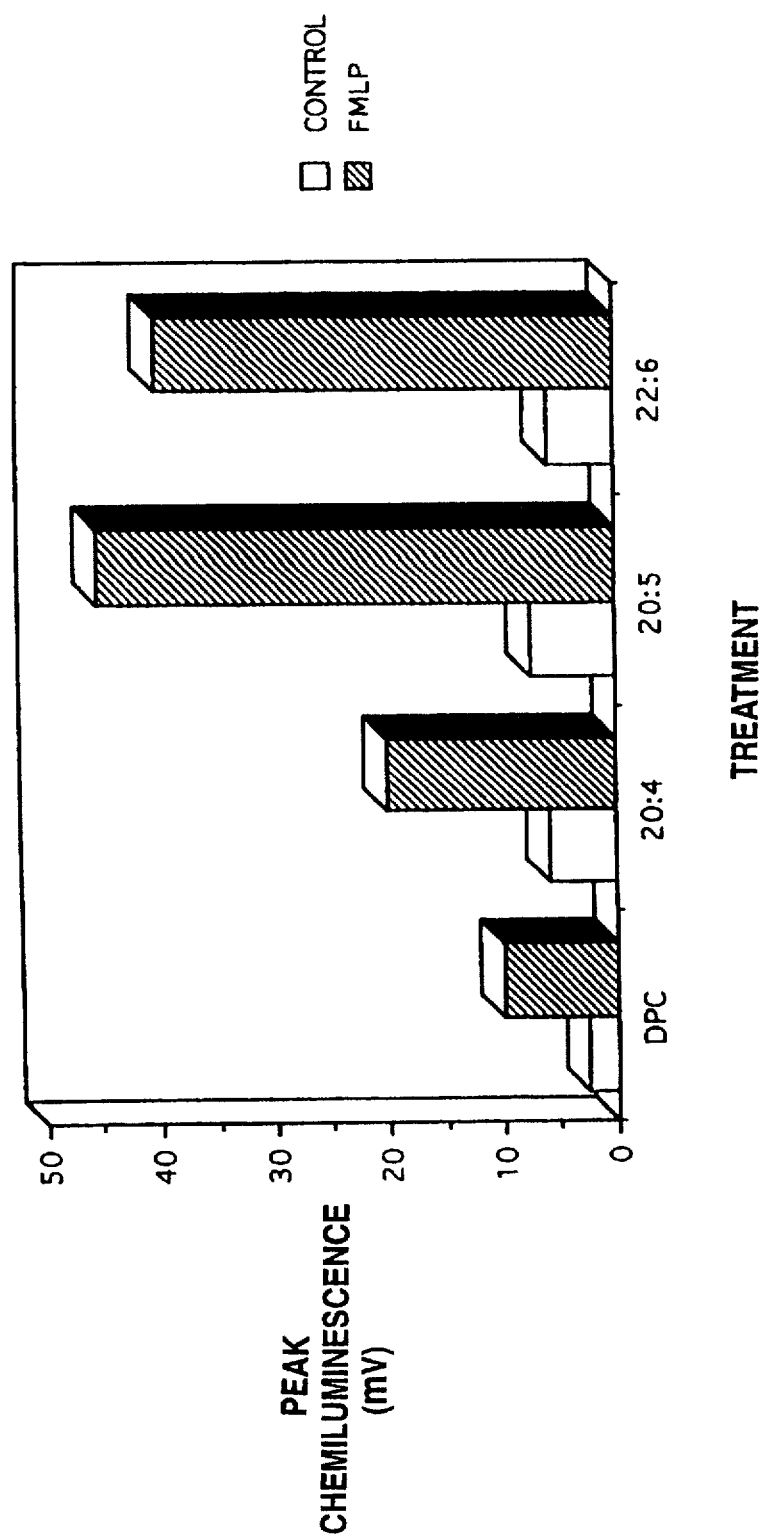
Figure 16:
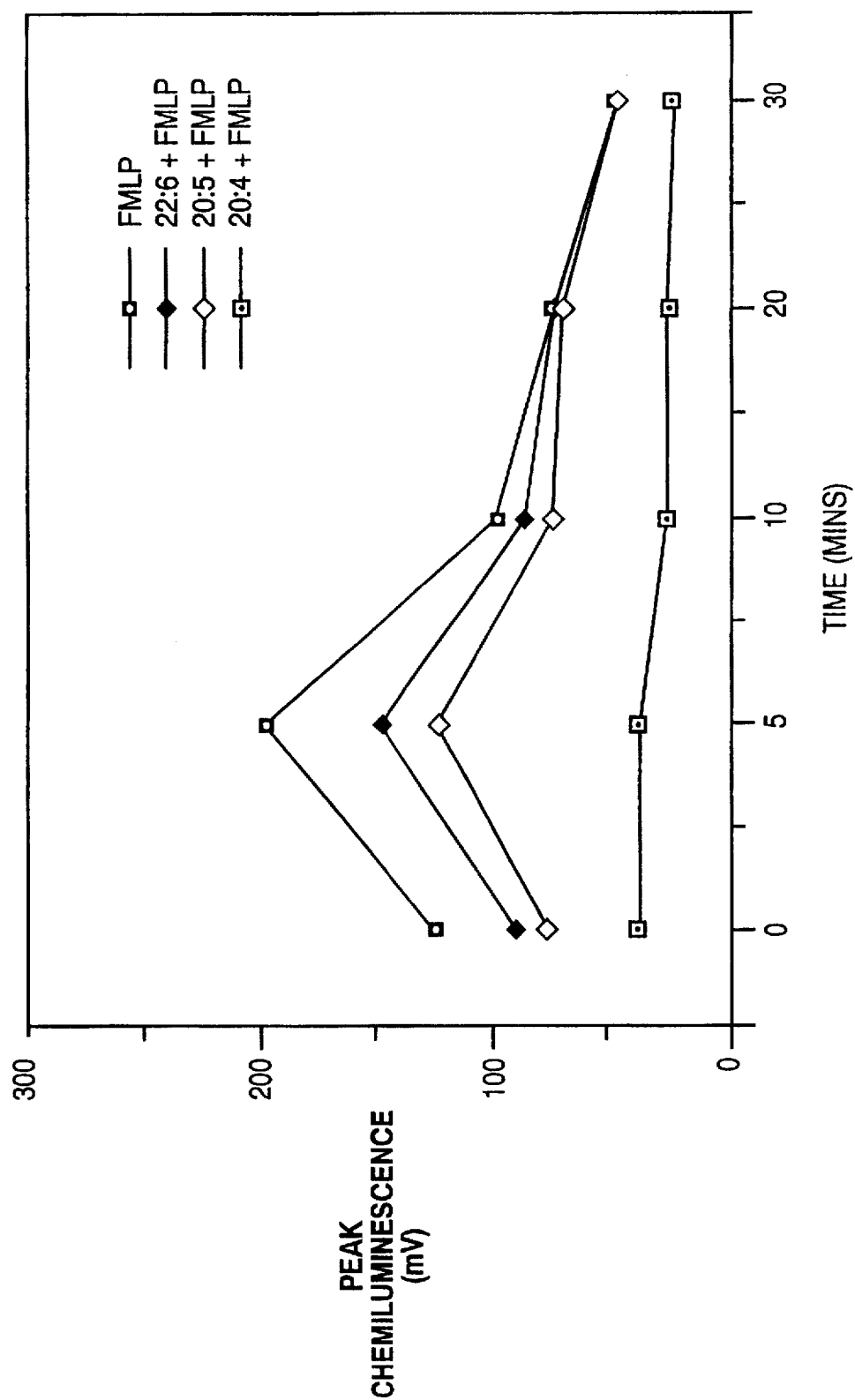
Figure 17:
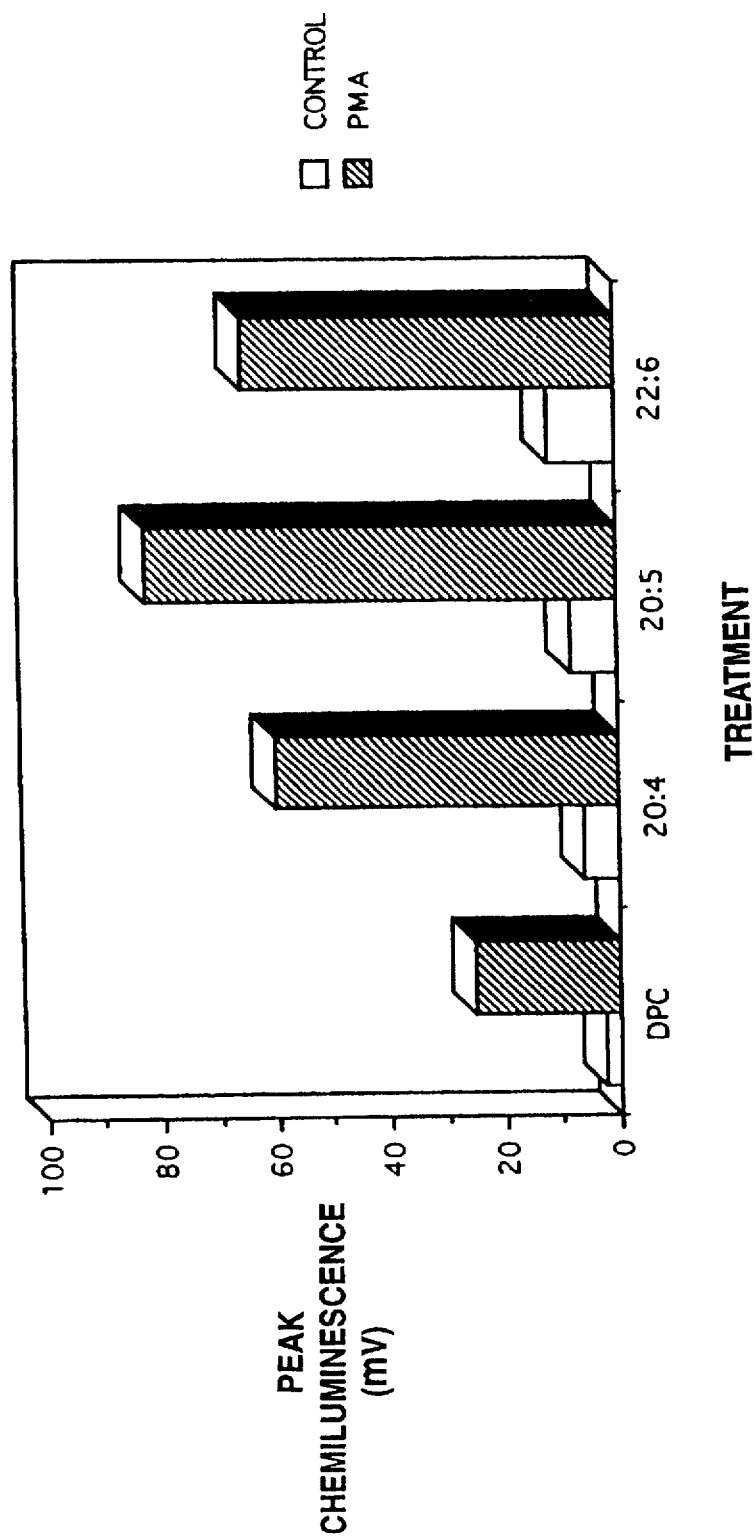
Figure 18:
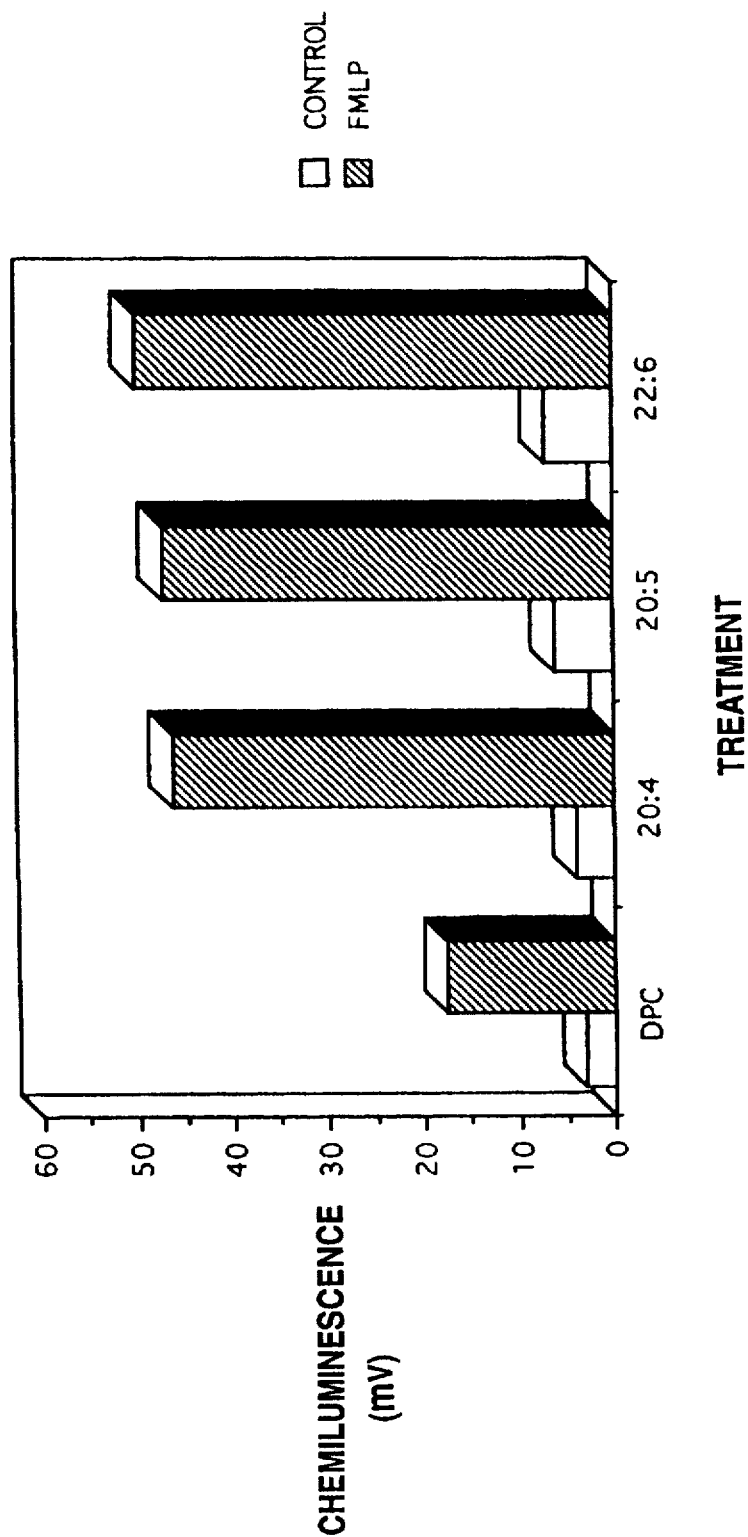
Figure 19:
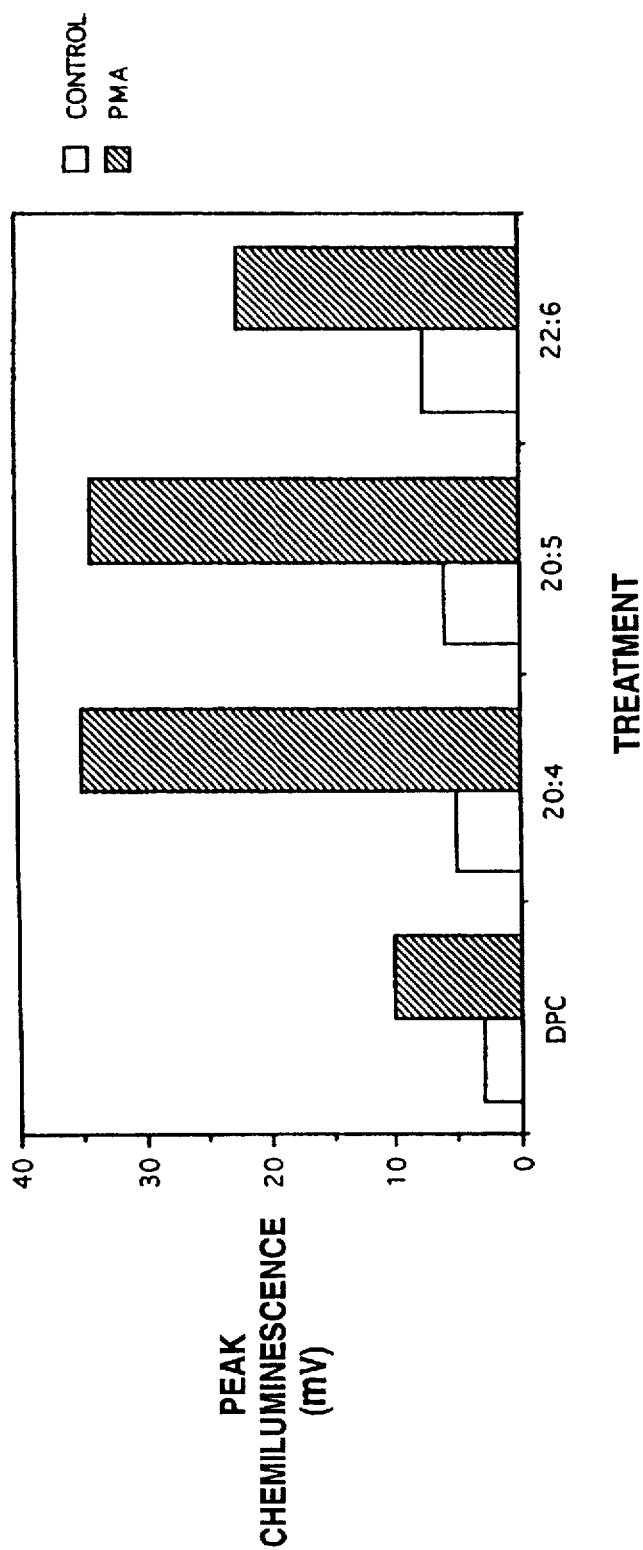
Figure 20:
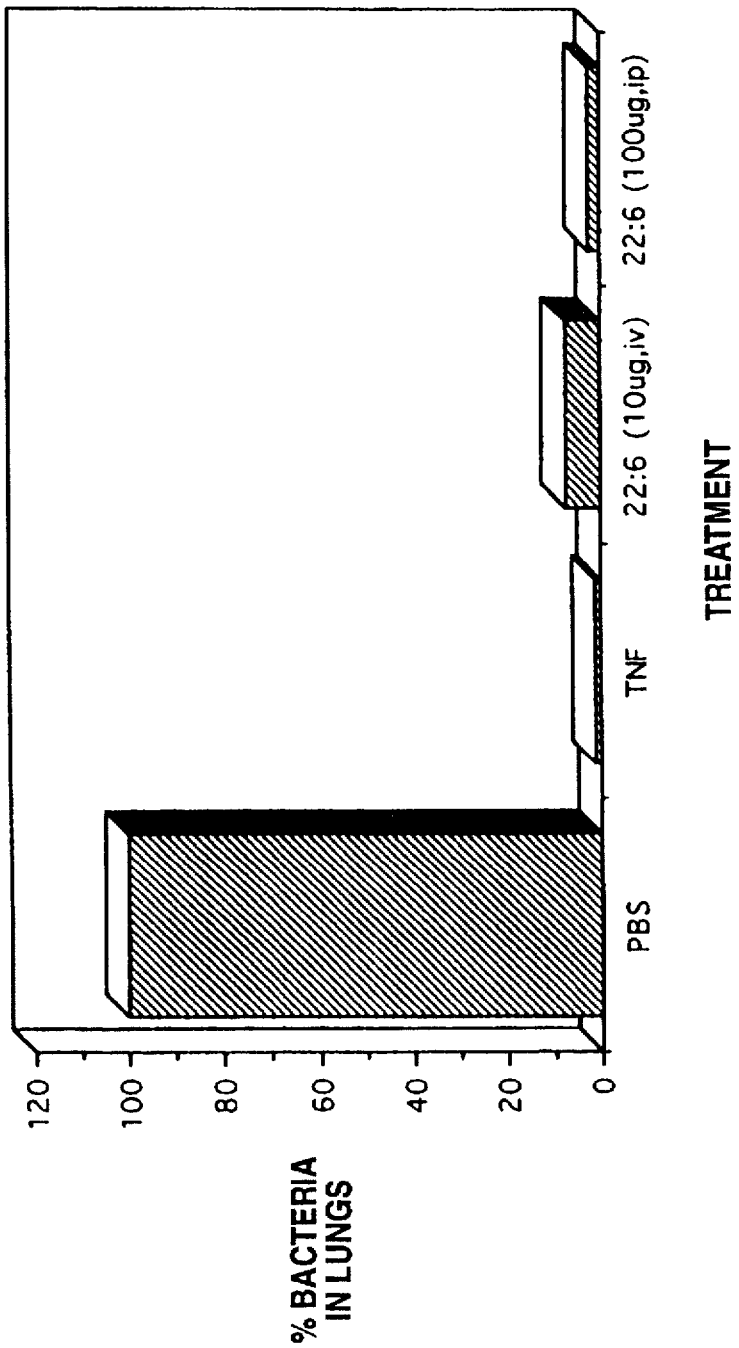
Figure 21:
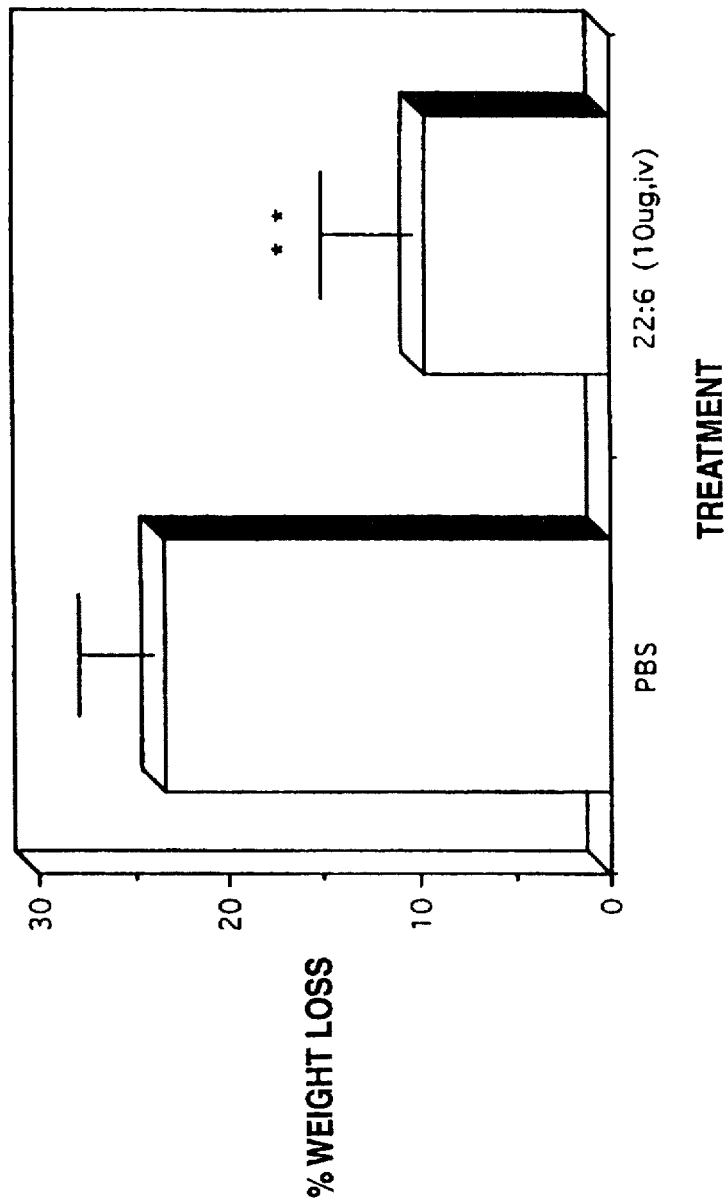

FIG. 10 shows effect of PUFAs on release of Vitamin $B_{12}$ binding protein. (Neutrophils were incubated for 30 min with the indicated concentrations of 22:6 (●, A), 22:6 methyl ester (♦, A), 20:4 (▲, B), 20:5 (■, B) or DPC alone (O). Results are from 5 to 6 separate experiments and have been represented as A and B for clarity. b,c,d indicated $p<0.02$, 0.01, 0.001 for neutrophils pretreated with fatty acids compared with DPC alone.);

FIG. 11 shows effect of PUFAs on release of β-glucuronidase by neutrophils. (Neutrophils were incubated for 30 min with the indicated concentrations of 22:6 (●, A), 22:6 methyl ester (♦, A), 20:4 (▲, B), 20:5 (■, B) or DPC alone (O). Results are from 5 to 6 separate experiments and have been represented as A and B for clarity. a,b indicate $p<0.05$, 0.02 for neutrophils pretreated with fatty acids compared with DPC alone.);

FIG. 12A shows release of vitamin $B_{12}$ binding protein from neutrophils stimulated with 33 μM PUFA;

FIG. 12B shows release of β glucuronidase from neutrophils stimulated with 33 μM PUFA;

FIG. 13 HUVEC prostaglandin $I_2$ synthesis. Neutrophils were pretreated for 30 min at $5\times10^6$/ml with 40 μM 20:4 or 20:5 (A) or $1\times10^6$/ml with 15 μM 20:4 or 20:5 (B<C). Control treatments contained appropriated concentrations of DPC alone. HUVEC were incubated for 30 min in the presence of these treated neutrophils as indicated before measurement of released 6KPGFIα. Other HUVEC incubations contained HBSS-HSA alone (-N), PMA (-N+PMA; $10^7$M), neutrophils alone (+N, $1\times10^6$), neutrophils+PMA (+N+PMA), or $H_2O_2$ alone (-N+$H_2O_2$; 100 μM) for 30 min. A,B and C represent 3 separate experiments each performed in duplicate;

FIG. 14 shows synergy between PUFA and TNF;

FIG. 15 The polyunsaturated FA 20:4, 20:5 and 22:6 stimulate the human monocyte respiratory burst as demonstrated in the lucigenin-dependent chemiluminescence assay. The PUFA prime for an enhanced responses to the bacterial peptide fMLP. 20:5 appears to be the most effective priming agent;

FIG 16 The polyunsaturated FA 20:4, 20:6 and 22:6 prime human monocytes for an enchanced response (reactive oxygen species to fMLP. Priming is optimal with 5 minutes pretreatment of the cells with PUFA (33 μM) prior to the addition of fMLP (100 nM). 20:5 appears to be the most effective priming agent;

FIG. 17 20:4, 20:5 and 22:6 prime human monocytes for an enhanced response to PMA. 20:5 is the most effective priming agent;

FIG. 18 Human macrophage respiratory burst is stimulated by 20:4, 20:5 or 22:6 treatment. Fatty acid pretreatment primes the macrophages for an enhanced response to fMLP;

FIG. 19 Fatty acids 20:4, 20:5 or 22:6 prime human macrophages for an enhanced response to the phorbol ester PMA;

FIG. 20 shows enhancement of removal of Psuedomonas from lungs;

FIG. 21 shows reduction of Psuedomonas infection-induced weight loss (p<0.01 compared to PBS); and FIG. 22 shows enhancements of anti-Candida effect of TNF in vivo. (p<0.01 compared to PBS. *p<0.05 compared to TNF alone)

MATERIALS AND METHODS

Preparation of Neutrophils

Heparinised blood from normal healthy individuals was layered onto Ficoll-Hypaque medium of density 1.114 and centrifuged at 600 g for 30–40 min at room temperature. The cells were washed three times in Hanks Balanced Salt Solution (HBSS). Preparations were of 96–99% purity was respect to white blood cells and were >99% viable as judged by their ability to exclude trypan blue. Red blood cell contamination was always less than 1 per neutrophil with platelets being generally absent.

Preparation of Fatty Acid Micelles and Pretreatment of Neutrophils

To overcome fatty acid insolubility in aqueous solution mixed dipalmitoyl phosphatidylcholine (DPC, 400 μg):fatty acid (100 μg) micelles were prepared in HBSS by sonication. Neutrophils were pretreated for 30 min at 37° C.

Malaria Growth Inhibition Assay

Aliquots of RBC ($5\times10^6$ with 3–5% parasitaemia) were mixed with neutrophils ($10^6$) in the wells of a 96-well microtitre plate and then incubated for 2 hr at 37° C. in 5% $CO_2$ in air before adding 1 mCi of 3H-hypoxanthine. The plates were then incubated overnight. Individual well contents were collected onto glass filter paper and incorporated $^3H$ measured in a liquid scintillation counter. Percent growth inhibition of the parasite was then calculated.

Measurement of Neutrophil Chemiluminescence

To 100 μl of neutrophils ($1\times10^6$) in HBSS was added 100 μl of fatty acid micelles or DPC alone and an additional 300 μl of HBSS. This was followed immediately by the addition of 500 μl of lucigenin (0.25 mg/ml in PBS and the resulting light output (mV) measured over time in a luminometer. Experiments were performed in triplicate with cells from a separate individual and values presented represent peak values of the responses.

Measurement of Degranulation

Degranulation was determined by measuring vitamin B12 binding protein (as described by Gottlaib et al, 1965, Blood 25:875–883) and β-glucuronidase release (as described by Kolodeney and Mumford, 1976, Clin. Chem. Acta 70:247–257).

Endothelial Cell Procoagulant Assay

Human umbilical vein endothelial cells (HUVEC) were treated with fatty acid (100 μM) for 72 hours prior to being scrape harvested, freeze-thawed and sonicated. 100 ml of the cell lysates were then placed in a tube containing platelet-poor plasma (100 μl) and calcium chloride (200 mM, 100 μl) and the time for coagulation to occur was measured at 37° C.

Neutrophil-Mediated Endothelial Cell Detachment

Neutrophils were pre-treated at $5\times10^6$ cells/ml with 40 μM fatty acid for 30 min. HUVEC were incubated for 3 hours in the absence or presence of the pre-treated neutrophils. % $^{51}$chromium was determined in supernatant (detached, lysed) and compared to total.

$PGI_2$ Production

Fatty acid-treated neutrophils were incubated with HUVEC for 30 min. The $PGI_2$ content of supernatants was then measured determining the level of its spontaneous hydrolysis product 6-keto-prostaglandin Flα using a scintillation proximity assay system (Amersham).

Bactericidal Assay

Human neutrophils ($1\times10^6$), purified as described above, were mixed with the bacteria Staphylococcus aureus ($1\times10^6$) in the presence of pooled human AB serum for varying periods at 37°. Samples (50 μl) were taken at t=0, 1, 2 hours post mixing and diluted in 10 mls distilled water. 50 μl of this dilution was then plated onto blood agar plates. The results are expressed as % bacteria surviving as determined by the following formula:

$$\% \text{ survival} = 100 - \frac{t = 0 \text{ counts} - t = 2 \text{ hr counts}}{t = 0 \text{ counts}}$$

Effects of PUFA on neutrophil mediated bactericidal activity were determined by the addition of 33 μm PUFA to the incubation mix.

Figure 1:
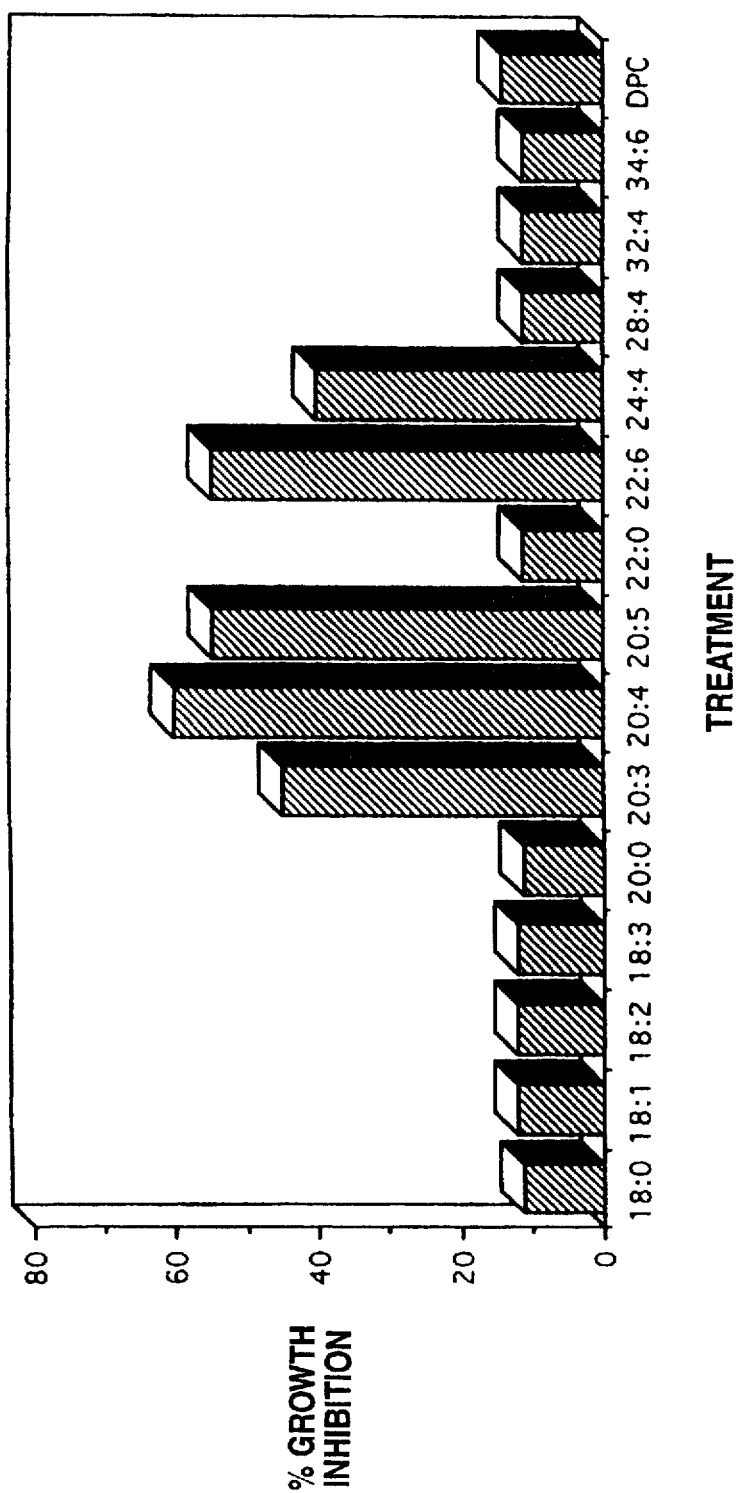
FIG. 1 shows % growth inhibition of malarial parasites by neutrophils stimulated with various PUFAs.
Figure 2:
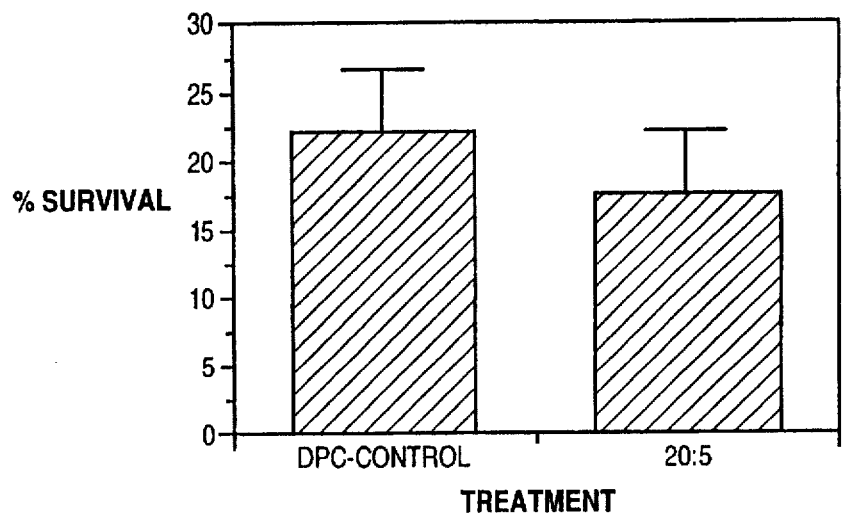
FIG. 2 shows bactericidal activity of C20:4(n-6) stimulated neutrophils against *S. aureus;*
Figure 3:
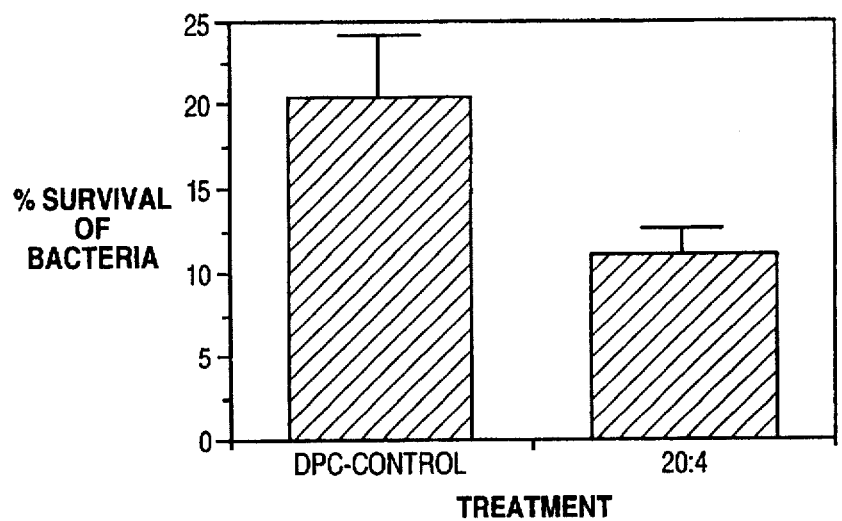
FIG. 3 shows bactericidal activity of C20:5(n-3) stimulated neutrophils against *S. aureus;*
Figure 4:
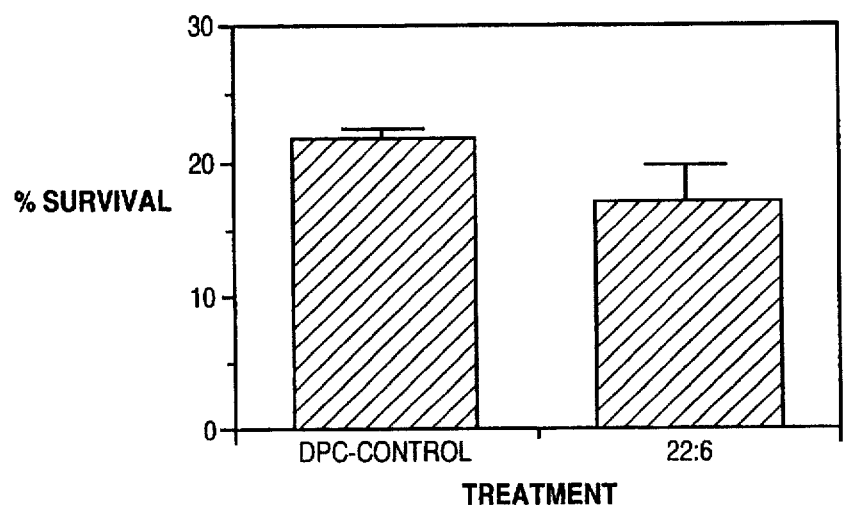
FIG. 4 shows bactericidal activity of C22:6(n-3) stimulated neutrophils against *S. aureus;*
Figure 5:
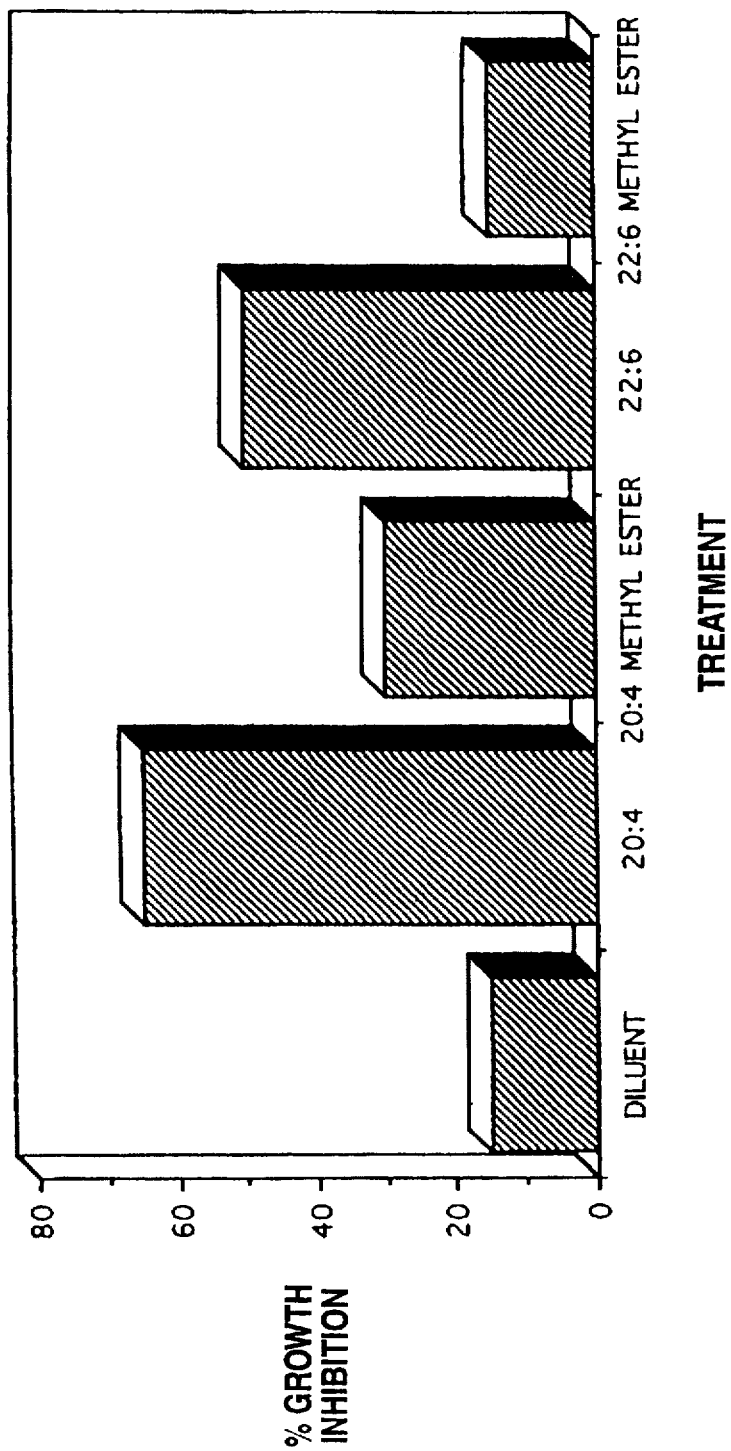
FIG. 5 shows lack of neutrophil stimulatory activity of PUFA methyl esters in inhibition of malaria parasite growth.
Figure 6:
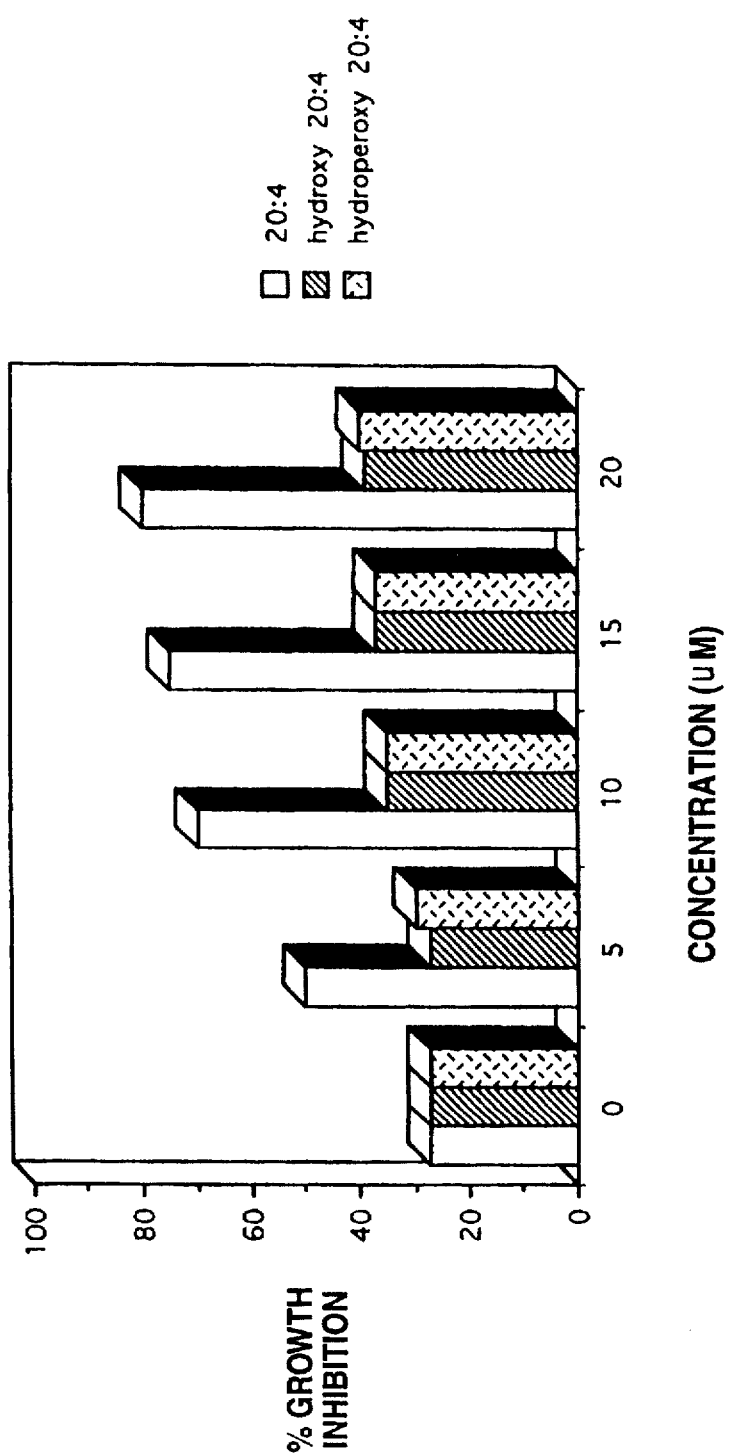
FIG. 6 shows lack of activity of hydroxy and hydroperoxy PUFAs in stimulating antimalarial activity of neutrophils.
Figure 7:
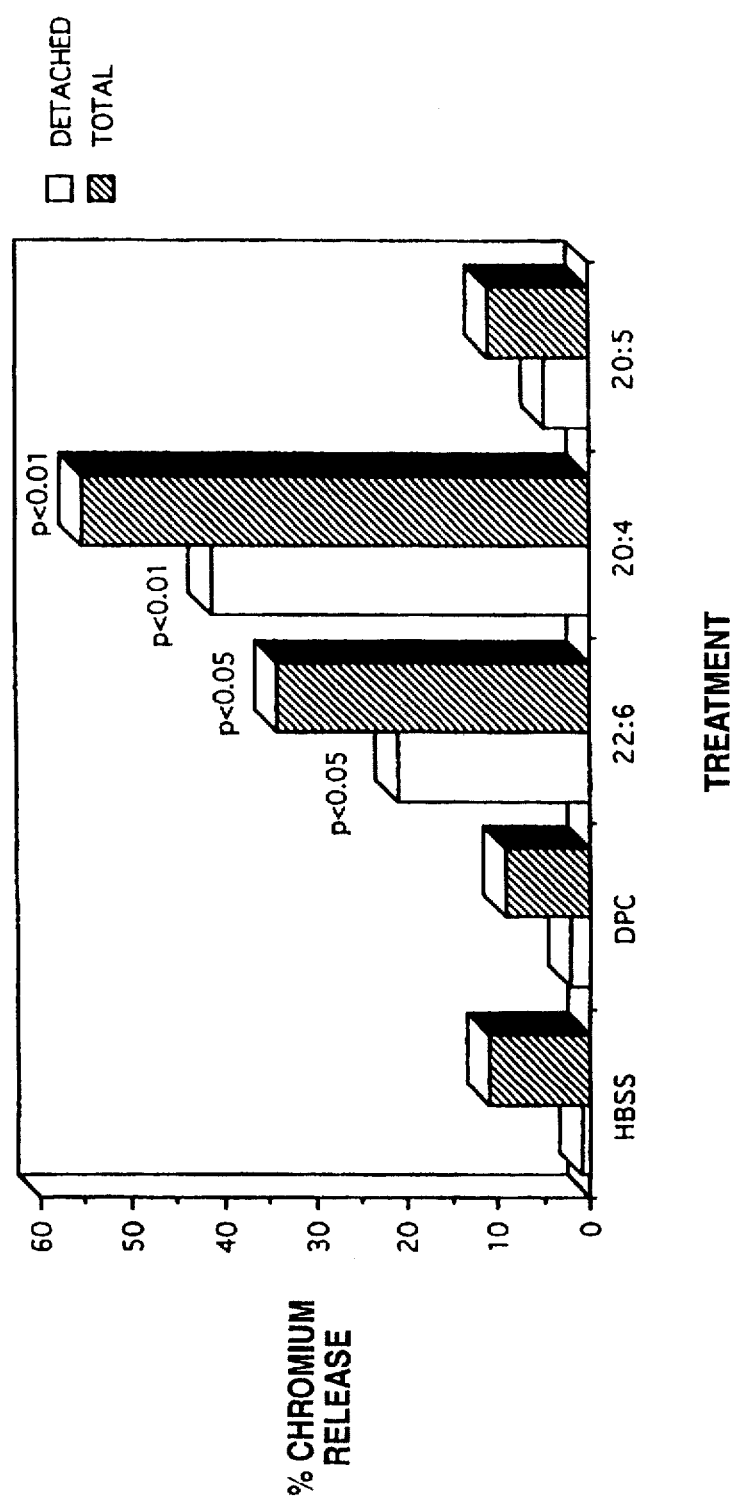
FIG. 7 shows neutrophil mediated endothelial cell damage as measured by cell detachment.
Figure 8:
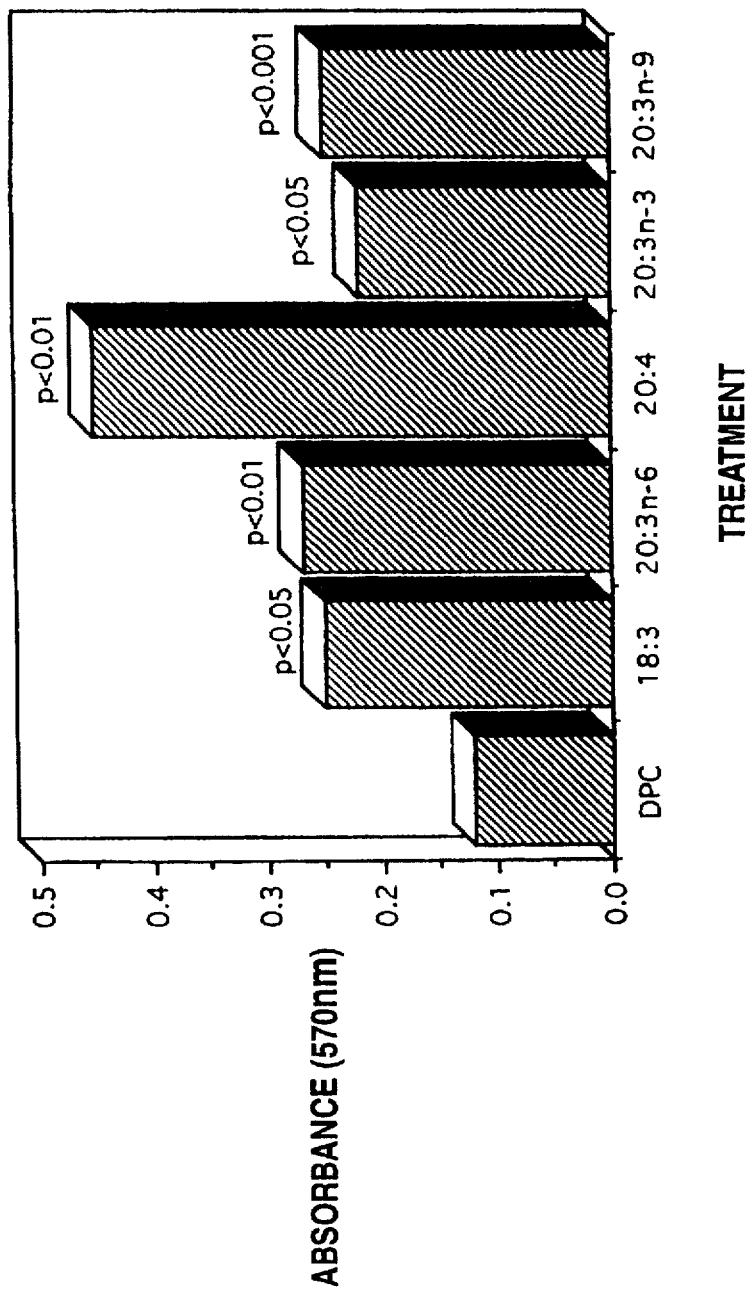
FIG. 8 shows neutrophil adherence to endothelial cell monolayers.

Preferred polyunsaturated fatty acids for enhancement of neutrophil-mediated killing of malaria parasites are: 20:3, (n-6); 20:4, (n-6); 20:5, (n-3); 22:6, (n-3); 24:4, (n-6) (FIG. 1). Neutrophils activated by 20:4, 20:5 and 22:6 were also found to have increased bactericidal activity against S. aureus as shown in FIGS. 2–4. The free fatty acid is functional but the methyl ester form is inactive (FIG. 5) as are the hydroxy and hydroperoxy forms (FIG. 6) indicating the importance of the carboxy region of the molecule for functional activity. Of these fatty acids only 20:4, (n-6) and 22:6, (n-3) (although not as potently as 20:4) initiated neutrophil-mediated endothelial cell damage as measured by cell detachment while 20:5, (n-3) did not induce endothelial cell damage (FIG. 7). Similarly 20:4 stimulates neutrophil adherence to endothelial cell monolayers while other PUFA such as 18:3γ (n-6) and 20:3 do not, despite their ability to stimulate the respiratory burst of neutrophils (FIGS. 8 & 9). Treatment of neutrophils with 20:5 (n-3) 20:3 (n-6) and 18 C PUFA results in the selective release of a vitamin B12 binding protein from specific granulas but not β-glucuronidase from azurophilic granules which contain enzymes such as elastase and may provide in part an explanation for the observed differences between 20:4 and 20:5 in mediating endothelial cell detachment since neutrophils treated with 20:4 release both vitamin $B_{12}$ binding protein and β-glucuronidase indicating release of azurophilic granule contents including elastase (FIGS. 10, 11 and 12). The PUFA were not able to induce significant procoagulant activity by endothelial calls (Table 1).

TABLE 1

Failure of PUFA to Induce Procoagulant Activity on Endothelial Cells.

| Treatment | Clotting Time (sec) |
| --- | --- |
| Control | 86.2 +/- 2.4 |
| 20:4 | 83 +/- 3.7 |
| 20:5 | 90.7 +/- 3.8 |
| 22.6 | 87.2 +/- 2.0 |

Production of $PGI_2$, another proinflammatory molecule was induced by 20:4 but not by 20:5 (FIG. 13). Neutrophil-stimulatory properties of the PUFA were synergistic with TNF (FIG. 14) and may be synergistic with fragments of the TNF molecule such as peptides 308, 309, 395 and 419. Synergism between PUFA and other mediators such as GM-CSF would also be expected from our observations with TNF/PUFA treatment of neutrophils.

Measurement of Neutrophil Chemiluminescence

To 100 µl of neutrophils ($1\times10^6$) in HBSS was added 100 µl of fatty acid (final concentration 10 µl/ml) and an additional 300 µl of HBSS. This was followed immediately by the addition of 500 µl of lucigenin (0.35 mg/ml in PBS and the resulting light output (mV) measured over time in a luminometer. Experiments were performed in triplicate with cells from a separate individual and values presented represent peak values of the responses.

The ability of 19:2 (n-6) and 23:4 (n-6) to stimulate neutrophil respiratory burst is set out in Table 2.

TABLE 2

STIMULATION OF NEUTROPHIL RESPIRATORY BURST

| Treatment | Mean Chemiluminescence (mV) |
|---|---|
| HBSS | 103 |
| 19:2n – 6 (10 µl/ml) | 253 |
| 23:4n – 6 (10 µl/ml | 284 |

CHEMILUMINESCENCE

Chemiluminescence results with monocytes are shown in FIGS. 15–17 and in macrophages in FIGS. 18 & 19.

PSUEDOMONAS LUNG INFECTION MODEL

Balb/C mice (female, 8–10 weeks) were infected intratracheally with *Psuedomonas aeuroginosa* on agarose beads (150–300 CFU). All treatments were administered intraperitoneally in sterile pyrogen-free saline. Treatments commenced 24 hours prior to infection and were administered daily until the day of sacrifice. Three days post infection (day 5) the animals were sacrificed and bacteria in the lungs enumerated. The lungs were homogenized in sterile saline and ten-fold dilutions prepared. 50 µl of the suspension was then plated onto blood agar plates and incubated for 24 hours at 37° C. The number of colonies were counted. Results were expressed as 1 og CFU/gm lung and % of bacteria in the lungs relative to the saline treated control (FIG. 20). In addition, on each day the animals were weighed to gauge loss of body weight as a result of either treatment or infection (FIG. 21). At the doses shown here the treatments alone did not induce weight loss. The results were tested for statistical significance by one way ANOVA.

DISSEMINATED CANDIDA INFECTION IN MICE $5\times10^5$ CFU candida albicans were inoculated i.v. into Balb/C female mice 10–12 weeks. Mice were treated with either sterile pyrogen-free saline, human recombinant TNF (2.5 µg) or PUFA (10 µg) administered i.p. Treatment commenced on day of infection and continued with daily administration to two days post-infection. Degree of infection at time of sacrifice was determined by enumeration of Candida organisms in the kidney at time of sacrifice. The results were expressed as CFU/gram of kidney (FIG. 22). Statistical analysis was performed by one way ANOVA.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method of stimulating macrophage, neutrophil and/or monocyte function in a subject, the method comprising co-administering to the subject an effective amount of a free fatty acid selected from the group of 18 to 24 carbon chain length with 2 to 6 double bonds and TNF or a TNF fragment or GMCSF or interferon gamma.

2. A method of stimulating macrophage, neutrophil and/or monocyte function in a subject, the method comprising co-administering to the subject an effective amount of a free polyunsaturated fatty acid selected from the group consisting of 20:4(n-6), 20:3(n-6), 20:5(n-3), 22:6(n-3), 19:2(n-6), 18:3(n-6), 23:4(n-6) and 20:5(n-3) and TNF or a TNF fragment or GMCSF or interferon gamma.

3. A method of treating a subject having depressed macrophage, neutrophil and/or neutrophil function, the method comprising co-administering to the subject of an effective amount of a free polyunsaturated fatty acid selected from the group consisting of 20:4(n-6), 20:3(n-6), 20:5(n-3), 22:6(n-3), 19:2(n-6), 18:3γ(n-6), 23:4(n-6) and 24:4(n-6) and TNF or a TNF fragment or GMCSF or interferon gamma.

4. A method of treating a subject suffering from a microbial infection, the method comprising co-administering to the subject an effective amount of a free polyunsatured fatty acid selected from the group consisting of 20:4(n-6), 20:3(n-6), 20:5(n-3), 22:6(n-3), 19:2(n-6), 18:3γ(n-6), 23:4(n-6) and 24:4(n-6) and TNF or a TNF fragment or GMCSF or interferon gamma.

5. A method of treating a subject suffering from cystic fibrosis comprising co-administering to the subject an effective amount of a free polyunsaturated fatty acid selected from the group consisting of 20:4(n-6), 20:3(n-6), 20:5(n-3), 22:6(n-3), 19:2(n-6), 18:3γ(n-6), 23:4(n-6) and 24:4(n-6) and TNF or a TNF fragment or GMCSF or interferon gamma.

6. A method of treating a subject suffering from a granulomatous disease comprising co-administering to the subject an effective amount of a free polyunsaturated fatty acid selected from the group consisting 20:4(n-6), 20:3(n-6), 20:5(n-3), 22:6(n-3), 19:2(n-6), 18:3γ(n-6), 23:4(n-6) and 24:4(n-6) and TNF or a TNF fragment or GMCSF or interferon gamma.

7. A method as claimed in claim 4 in which the microbial infection is a parasitic infection.

8. A method as claimed in claim 7 in which the parasitic infection is a malarial infection.

9. A method as claimed in claim 4 in which the microbial infection is a bacterial infection.

10. A method as claimed in claim 9 in which the bacterial infection is a *S. aureus, P. aueruginosa, H. influenzae, Pneumocystis* or Pneumococcal infection.

11. A method as claimed in claim 4 in which the microbial infection is a fungal infection.

12. A method as claimed in claim 11 in which the yeast infection is a Candida infection.

13. A method as claimed in claim 3 in which the subject having depressed neutrophil function is suffering from acquired immune deficiency syndrome, cancer or alcohol-induced phagocytic cell deficiency.

14. A method as claimed in claim 6 in which the granulomatous disease is TB, Crohns Disease, sarcoidosis, leprosy, syphilis or mycobacterium avium complex.

15. A method as claimed in claim 1 in which the polyunsaturated fatty acid is 20:3(n-3).

* * * * *